United States Patent [19]
Khambay et al.

[11] Patent Number: 6,043,286
[45] Date of Patent: Mar. 28, 2000

[54] PESTICIDAL COMPOUNDS

[75] Inventors: Bhupinder Pall Singh Khambay, Southall; Duncan Batty, Kempston, both of United Kingdom

[73] Assignee: BTG International Limited, London, United Kingdom

[21] Appl. No.: 08/891,079

[22] Filed: Jul. 10, 1997

Related U.S. Application Data

[63] Continuation of application No. PCT/GB96/00041, Jan. 10, 1996.
[60] Provisional application No. 60/001,099, Nov. 13, 1995.

[30] Foreign Application Priority Data

Jan. 10, 1995 [GB] United Kingdom ............... 9500389
Jul. 4, 1995 [GB] United Kingdom ............... 9513584
Jul. 4, 1995 [GB] United Kingdom ............... 9513594

[51] Int. Cl.[7] ..................... A01N 35/06; A01N 33/02; C07C 50/12; C07C 50/00
[52] U.S. Cl. ................. 514/682; 514/681; 514/641; 514/712; 552/295; 552/298
[58] Field of Search ..................... 552/298, 295; 514/682, 681, 641, 712

[56] References Cited

U.S. PATENT DOCUMENTS

2,398,418 4/1946 Fieser ........................ 167/30
2,572,946 10/1951 Paulshock ................... 167/90

FOREIGN PATENT DOCUMENTS

0 002228 6/1979 European Pat. Off. .
0300218 1/1989 European Pat. Off. .
2323 676 4/1977 France .
2520739 11/1975 Germany .
WO 95/32176 11/1995 WIPO .

*Primary Examiner*—Alan L. Rotman
*Assistant Examiner*—Raymond Covington
*Attorney, Agent, or Firm*—Nixon & Vanderhye

[57] ABSTRACT

Pesticidal as a pesticide against whitefly, Lepidoptera and certain fungi is provided of compound of general formula (I)

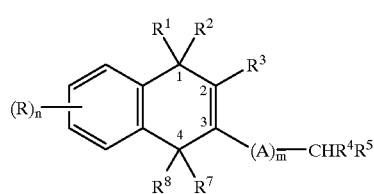

or a salt thereof is provided, in which n represents an integer from 0 to 4; m represents an integer 0 or 1;

each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group;

$R^1$ and $R^2$ each independently represent an optionally substituted alkoxy group or together represent a group $=O$, $=S$ or $=N-OR^9$, where $R^9$ represents a hydrogen atom or an optionally substituted alkyl group;

$R^3$ represents a hydroxyl group, or a group $-OL$ where L is a leaving group, or a group which in vivo is transformed into a group $-OL^1$ where $L^1$ is a leaving group;

$R^7$ and $R^8$ independently represent an optionally substituted alkoxy group or together represent a group $=O$, $=S$ or $=N-OR^9$, where $R^9$ is as previously defined;

wherein $R_4$ and $R_5$ independently represent a halogen atom or an optionally substituted alkyl or alkenyl group, or together with the interjacent carbon atom represent an optionally substituted cycloalkyl or cycloalkenyl ring; and A represents a straight or branched chain alkyl or alkenyl group, which may be optionally substituted, an acyclic carbon chain of which links the 3 position of the naphthalene ring shown and the moiety $-CHR^4R^5$ and wherein A does not include a quaternary carbon atom in that chain; and wherein the total number of carbon atoms in the longest carbon chain running from the 3-position of the naphthalene ring shown is no more than 8.

42 Claims, No Drawings

PESTICIDAL COMPOUNDS

This is a continuation of PCT application No. PCT/GB96/00041, filed Jan. 10, 1996 PCT application No. 60/001,099 filed Nov. 13, 1995.

The present invention relates to the use of certain 1,2,3,4-substituted naphthalene compounds as pesticides active, inter alia, against whitefly and certain fungi; to methods for preparation of these compounds; to compositions containing them and to use of the compounds and compositions for the control of whitefly, Lepidoptera and fungal pests.

U.S. Pat. No. 2,572,946 discloses a composition for the control of mites and aphids in which the active ingredient is a compound of the general formula (P1)

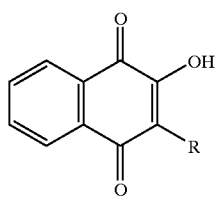

(P1)

where R is a radical, containing from 6 to 15 carbon atoms, selected from alkyl, cyclohexyl and cyclohexylalkyl groups; n-alkyl, iso-alkyl, alkylcycloalkyl and aralkyl groups being exemplified. No specific miticidal or aphicidal data is given for these compounds and thus no indication is given as to which of the many compounds is best or, indeed, whether these are useful for control of pests other than mites and aphids.

DE 2641343 A1 generically discloses compounds of the general formula (P2)

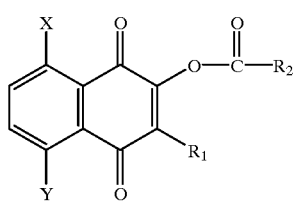

(P2)

in which $R_1$ is a straight, branched or cyclic $C_{8-14}$ alkyl group, $R_2$ is a straight or branched $C_{1-17}$ alkyl, $C_{2-17}$ alkenyl, $C_{3-6}$ cycloalkyl, $C_{1-4}$ alkoxy, —$CH_2OCH_3$, —$CH_2OCH_2CH_3$ or —CH═CH—COOH group, and X and Y represent a hydrogen, fluorine, chlorine or bromine atom or a methyl or methoxy group. These compounds are said to exhibit acaricidal and aphicidal activity but only compounds where $R_1$ is a linear $C_8$ or $C_{11-14}$ alkyl group are shown to have such activity.

U.S. Pat. No. 4,110,473 concerns a method for protecting plants from mites (acarids) which comprises treating the plant with a compound of the general formula (P3)

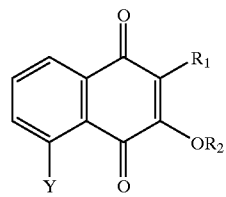

(P3)

where Y is hydrogen, fluorine, chlorine or bromine; $R_1$ is branched, cyclic or straight chain $C_{8-14}$ alkyl; $R_2$ is branched or straight chain $C_{1-12}$ saturated alkyl or $C_{3-12}$ unsaturated alkyl optionally substituted by one or two chlorine, bromine, methoxy or ethoxy substituents, or $C_{3-6}$ cycloalkyl.

GB 1553424 discloses compound of general formula (P3) wherein $R^2$ is H and $R^1$ is optionally substituted cyclohexyl, for use as an active agent for treatment of infection of cattle with theilerosis, while EP 0123238 and EP 0123230 relate to similar such compounds for use as anti-protozoan and anti-coccodiosis agents.

DE 3801743 A1 generically discloses compounds of the general formula (P4)

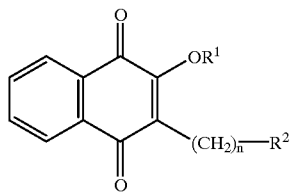

(P4)

in which n is 0 to 12, $R^1$ represents hydrogen or an optionally substituted alkyl, aralkyl, alkylcarbonyl, (hetero) arylcarbonyl, alkoxycarbonyl, alkylsulphonyl or arylsulphonyl group, and $R^2$ represents a haloalkyl, optionally substituted (hetero)aryl or substituted cycloalkyl group. These compounds are said to exhibit acaricidal and fungicidal activity.

Ten compounds are specifically disclosed of formula (P4) in which n is 0, $R^1$ is a hydrogen atom and $R^2$ is a 4-(t-butyl)cyclohexyl, 4-(trimethylsilyl)cyclohexyl, 4-(cyclohexyl)-cyclohexyl, 2-trifluoromethylcyclohexyl or 3,5-di(trifluoromethyl)-cyclohexyl group or n is 0, $R^1$ is an ethanoyl group and $R^2$ is a 4-(t-butyl)cyclohexyl, 4-(cyclohexyl)cyclohexyl, 2- or 3-trifluoromethylcyclohexyl or 3,5-di(trifluoromethyl)-cyclohexyl group. Of these, acaricidal activity is demonstrated for two compounds of formula (P4) in which n is 0, $R^1$ is a hydrogen atom and $R^2$ is a 4-(t-butyl)cyclohexyl or 4-(trimethylsilyl)-cyclohexyl group.

EP 0077550 discloses compounds of general formula (P5)

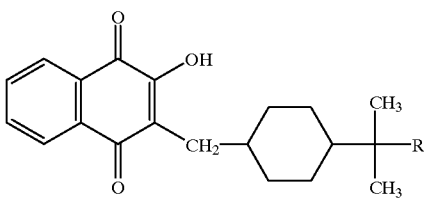

(P5)

in which R is an alkyl group of from 1 to 10 carbon atoms and describes their use in veterinary formulations, particularly for prophylaxis against protozoan infection.

Copending international application No. PCT/GB95/00953 relates to naturally occurring compounds of the general formula (P6)

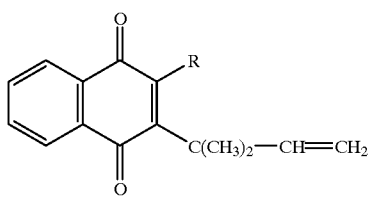

(P6)

in which R represents a hydrogen atom or a hydroxyl or an ethanoyloxy group, and relates to their use as pesticides, especially fungicides, insecticides and/or acaricides. These compounds were previously disclosed as plant metabolites by Chamy el al., (1993) Bol. Soc. Chil. Quim. 38 187–190.

DE 2520793 A1 generically discloses compounds of the general formula (P7)

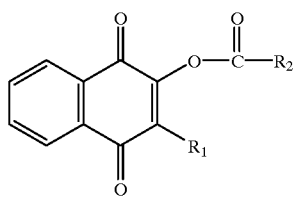

(P7)

in which $R_1$ is a straight, branched or cyclic $C_{8-14}$alkyl group, and $R_2$ is a straight or branched $C_{1-6}$ alkyl group or a $C_{3-6}$ cycloalkyl group. These compounds are said to exhibit acaricidal and aphicidal activity but only compounds where $R_1$ is a linear $C_{11}$ or $C_{12}$ alkyl group are shown to have such activity.

EP 0002228 generically discloses compounds of the general formula (P8)

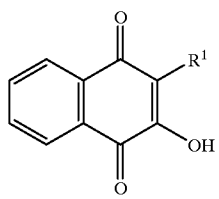

(P8)

in which $R^1$ is a substituted or unsubstituted $C_{3-12}$ cycloalkyl group. The compounds are said to be active against Theileria in cattle and sheep, though only the compound in which $R^1$ is cycloheptyl is shown to have such activity.

Numerous 2-hydroxy or 2-alkoxy 3-substituted naphthalene-1,4-dione compounds have been disclosed by Fieser et al. and other workers for use in treatment of malaria (see eg. U.S. Pat. No. 2,553,647, U.S. Pat. No. 3,578,685 and JACS (1948) Vol 70 pp. 3151, 156–3165) or as antitumour agents (see FR 2085660). These include a number of 3-isoalkyl substituted compounds. In U.S. Pat. No. 2,398,418, Fieser shows how to prepare 2,3-disubstituted naphthalene-1,4-dione compounds from the corresponding 2-substituted compound.

The present inventors have determined that many of the prior art naphtlloquinones do not have high activity against whitefly, and particularly that most of the aphicidal and acaricidal compounds specifically disclosed in the prior art have disappointing efficacy when tested against whitefly of resistant and susceptible types.

The present inventors have now determined that certain synthetic naphthoquinones and related 1,4 derivatized compounds have advantageous pesticidal properties over those disclosed for such use in the prior art, particularly as applied to treatment of whitefly. Preferred synthetic compounds for the use of the invention have excellent pesticidal activity against, inter alia, whitefly and/or fungi, with most preferred compounds also showing good activity against mites and/or aphids. The compounds identified by the present inventors have particular use against strains of whitefly and fungi that have become resistant to one or more of the currently commercially available pesticides.

According to a first aspect of the present invention there is provided the use of a compound of general formula (I)

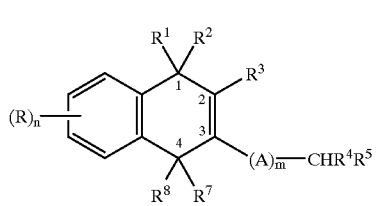

(I)

or a salt thereof as a pesticide against whitefly, Leptidoptera and/or fungal pests, in which n represents an integer from 0 to 4; m represents an integer 0 or 1;

each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group;

$R^1$ and $R^2$ each independently represent an optionally substituted alkoxy group or together represent a group =O, =S or =N—OR$^9$, where R$^9$ represents a hydrogen atom or an optionally substituted alkyl group;

$R^3$ represents a hydroxyl group, or a group —OL where L is a leaving group, or a group which in vivo is transformed into a group —OL$^1$ where L$^1$ is a leaving group;

$R^7$ and $R^8$ independently represent an optionally substituted alkoxy group or together represent a group =O, =S or =N—OR$^9$, where R$^9$ is as previously defined; and wherein $R_4$ and $R_5$ independently represent a hydrogen or halogen atom or an optionally substituted alkyl or alkenyl group, or together with the interjacent carbon atom represent an optionally substituted $C_{4-8}$ cycloalkyl or cycloalkenyl ring; and A represents a straight or branched chain alkyl or alkenyl group, which may be optionally substituted, preferably with halogen, an acyclic carbon chain of which links the 3 position of the naphthalene ring shown and the moiety —CHR$^4$R$^5$ and wherein A does not include a quaternary carbon atom in that chain; and wherein the total number of carbon atoms in the longest carbon chain running from the 3- position of the naphthalene ring shown is no more than 8.

Preferably the total number of carbon atoms in the longest chain running from the 3-position is from 4 to 8, more preferably from 5 to 7. Where the number of carbon atoms is restricted to 1 or 2 whitefly activity is lost but antifungal activity remains high. Where —CH $R^4R^5$ form a carbocyclic ring this is preferably directly attached to the naphthalene 3-position as increasing numbers of carbon atoms between the naphthalene ring and the naphthalene ring result in decreased whitefly activity.

The present use particularly provides compounds for use against whitefly, particularly of species of Bemisia, and/or fungi, particularly of species of Rhizoctonia, Aspergillus and Pyricularia eg. *R. solani, P. oryzae* and *A. niger*, that have developed resistance to one or more commercially available non-naphthoquinone based pesticides, and most preferably for use against whitefly of species *Bemisia tabaci* such as Ned 1/2, Ned 7, and Pak types; these having been determined by the present inventors to be particularly susceptible to the pesticidal actions of the presently identified compounds as compared to those of, for example, those compounds specifically tested in U.S. Pat. Nos. 2,572,946, 4,110,473 and DE 2641343. Although DE 3801743 lists some of the presently used compounds per se and describes them as useful against many different species of insect and fungi, no indication is given as to the significantly advantageous application of such compounds to combatting whitefly.

When the compounds of formula I contain a group defined as an alkyl, alkenyl or alkynyl substituent group otherwise undefined, this may be linear or branched and may contain up to 12, preferably up to 6 and especially up to 4, carbon atoms. A cycloalkyl or cycloalkenyl group may contain from 3 to 10, but most preferably contains 5 to 8 carbon atoms. An aryl group may be any aromatic hydrocarbon group, especially a phenyl or naphthyl group. An aralkyl group may be any alkyl group as defined above which is substituted by an aryl group as defined above, especially a benzyl group, or may be an aryl group substituted by an alkyl group.

When any of the foregoing substituents are designated as being optionally substituted, the substituent groups which are optionally present may be any one or more of those customarily employed in the development of pesticidal compounds and/or the modification of such compounds to influence their activity, persistence, penetration or other property. Specific examples of such substituents include, for example, halogen atoms, nitro, cyano, hydroxyl, alkyl, alkenyl, haloalkyl, haloalkenyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, phenyl and benzyl groups. Typically, 0–3 substituents may be present. When any of the foregoing substituents represents or contains an alkyl substituent group, this may be linear or branched and may contain up to 12, preferably up to 6, and most preferably up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, alkenyl, haloalkyl, haloalkenyl, alkoxy or haloalkoxy groups. Preferably, the aryl moiety is a phenyl moiety and the cycloalkyl moiety contains from 3 to 8, preferably 4 to 7, carbon atoms.

It is preferred that R, if present, represents a halogen atom or a nitro, cyano, hydroxyl, $C_{1-4}$ alkyl, $C_{1-4}$ haloalkyl, $C_{2-4}$ alkenyl, $C_{2-4}$ haloalkenyl, $C_{1-4}$ alkoxy, $C_{1-4}$ haloalkoxy, $C_{1-4}$ alkylamino, di-$C_{1-4}$ alkylamino, $C_{1-4}$ alkoxycarbonyl, $C_{1-4}$ alkylthio, $C_{1-4}$ alkylsulphinyl or $C_{1-4}$ alkylsulphonyl group.

More preferably, R, if present, represents a halogen atom or a $C_{1-4}$ alkyl, $C_{1-4}$ haloalkyl, $C_{2-4}$ alkenyl, $C_{2-4}$ haloalkenyl, $C_{1-4}$ alkoxy or $C_{1-4}$ haloalkoxy group.

Preferably, n is 0, 1 or 2 and it is especially preferred that n is 0.

It is also preferred that $R^1$ and $R^2$ each independently represent a $C_{1-4}$ alkoxy group, especially a methoxy group, or together represent a group =O or =N—$OR^9$, where $R^9$ represents a hydrogen atom or a $C_{1-4}$ alkyl, especially a methyl, group. It is especially preferred that $R^1$ and $R^2$ are both methoxy or together represent a group =O.

When $R^3$ is a group —OL where L is a leaving group, or a group which in vivo is transformed into a group —$OL^1$ where $L^1$ is a leaving group, the leaving group may be any group customarily employed as a leaving group. It is preferred that the leaving group is such that the $pK_a$ value of the acid LOH or $L^1OH$ in water is from 1 to 7, more preferably from 1 to 6 and especially from 1 to 5.

When $R^3$ represents a group which in vivo is transformed into a group —$OL^1$ where L is a leaving group, it is preferred that the transformation is carried out in a plant to be protected or a pest to be combated, preferably by action of enzymes within the plant or pest. For instance, if $R^3$ represents a β-acid group, such as —O—$CH_2CH_2$CO—OH where —$CH_2CH_2$CO—OH is not a leaving group, it may be subjected to enzymatic oxidation in vivo to form a group —O—CO—$CH_2$—CO—OH, e.g. by a β-oxidase, where —CO—$CH_2$—CO—OH is a leaving group.

Preferably, $R^3$ represents a group —$OR^{10}$ where $R^{10}$ represents a hydrogen atom, an optionally substituted alkyl, alkenyl, aryl or aralkyl group or a group —CO—$R^{11}$, —CO—O—$R_{11}$, —$SOR^{11}$, —$SO_2$—$R^{11}$, —$P(X)(OR^{12})$ $(OR^{13})$, —$P(X)(R^{12})(OR^{13})$, —$P(OR^{12})(OR^{13})$ or —$P(R^{12})$ $(OR^{13})$ where $R_{11}$ represents a hydrogen atom, an optionally substituted alkyl, alkenyl, aryl or aralkyl group or a group —$NR^{12}R^{13}$; $R^{12}$ and $R^{13}$ independently representing a hydrogen atom or an optionally substituted alkyl group and X represents an oxygen or sulphur atom. Where $R^{10}$ or $R^{11}$ represents an optionally substituted aryl or aralkyl group, it is preferred that the aryl group or moiety is a phenyl group or moiety and that the optional substituents are selected from halogen atoms, nitro and $C_{1-4}$ alkyl groups. Substitution at the 4-position of the phenyl ring is particularly preferred. For the purposes of $R^3$, the term optionally substituted includes, e.g. substitution with silicon containing groups, e.g. trialkylsilyl groups such as trimethylsilyl, as a substituent on $R^{10}$, $R^{11}$ or $R^{12}$.

Preferably $R^3$ represents a hydroxyl group or a group —O—CO—$R^{11}$ or —O—CO—$OR^{11}$ where $R_{11}$ represents a hydrogen atom or a $C_{1-12}$ alkyl, $C_{1-12}$ haloalkyl, $C_{1-12}$ hydroxyalkyl, $C_{1-12}$ carboxylalkyl, phenyl or benzyl group.

It is particularly preferred that $R^3$ represents a group —OH or —O—CO—$R^{11}$, where $R_{11}$ represents a hydrogen atom or a $C_{1-6}$ alkyl, $C_{1-6}$ haloalkyl, phenyl or benzyl group. Most preferred for $R^{11}$ is a methyl, ethyl, propyl or butyl group.

Preferably, $R^7$ and $R^8$ independently represent a $C_{1-4}$ alkoxy group or together represent a group =O or =N—$OR^9$, where $R^9$ represents a hydrogen atom or a $C_{1-4}$ alkyl group, but it is especially preferred that $R^7$ and $R^8$ are both methoxy or together represent a group =O.

It will be realised by those skilled in the art that compounds wherein $R^1$ and $R^2$, and $R^7$ and $R^8$ are each alkoxy, or in pairs =S or a group $NOR^9$, will be potential biological precursors for the corresponding naphthoquinones; the naphthoquinones being the preferred compounds of the invention.

Preferably, $R^4$ and $R^5$ each independently represent hydrogen, or a $C_{1-7}$ alkyl, $C_{1-7}$ haloalkyl, $C_{2-7}$ alkenyl or $C_{2-7}$ haloalkenyl group or, together with the interjacent carbon atom, represent a $C_{4-8}$ cycloalkyl or cycloalkenyl ring which is optionally substituted with substitutents selected from halogen and methyl, ethyl, ethenyl, halomethyl, haloethyl and haloethenyl groups. More preferably $R^4$ and $R^5$ are independently selected from $C_{1-4}$ alkyl, $C_{1-4}$ haloalkyl, $C_{2-4}$ alkenyl and $C_{2-4}$ haloalkenyl groups or form a ring.

The compounds of formula I may form salts, e.g. when $R^3$ represents a hydroxyl group. Suitable bases for forming such salts include inorganic bases, such as sodium hydroxide, potassium hydroxide or sodium carbonate, and organic bases, for example tertiary amines such as triethylamine and cyclic amines such as pyrrolidine.

It will be appreciated by those skilled in the art that many of the compounds for the use of the present invention will exist as different geometric isomers and diastereomers. The invention thus includes both the individual isomers and mixtures of these.

In a first preferred distinct group of compounds for the use of the first aspect of the invention the moiety —CH $R^4R^5$ is provided immediately adjacent the naphthalene ring wherein $R^4$ and $R^5$ independently represent a hydrogen, halogen or an optionally halo-substituted alkyl or alkenyl group.

In this first preferred group compounds of general formula (II)

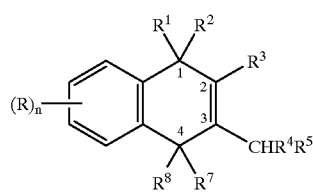

(II)

or a salt thereof are used in which R, $R^1$, $R^2$, $R^3$, $R^7$ and $R^8$ and n are as defined for formula I and $R^4$ and $R^5$ independently represent a hydrogen or halogen or an alkyl or alkenyl group that is optionally halo-substituted while remaining within the limits for carbon chain length set out for formula I.

More preferred compounds of the general formula (II) are those where n is 0, $R^1$ with $R^2$, and $R^7$ with $R^8$ are both =O; wherein one of $R^4$ and $R^5$ represents hydrogen, $C_{1-7}$ alkyl or $C_{1-7}$ haloalkyl or a $C_{2-7}$ alkenyl or $C_{2-7}$ haloalkenyl group and the other is independently selected from $C_{1-7}$ alkyl or $C_{1-7}$ haloalkyl or a $C_{2-7}$ alkenyl or $C_{2-7}$ haloalkenyl group. $R^3$ is preferably —OH, —O—CO—$R^{11}$ or —O—CO—O—$R^{11}$ where $R_{11}$ is $C_{1-3}$ alkyl; and most preferably —OH. Most preferably —CH$R^4R^5$ contains from 2 to 5 carbons.

It is found by the inventors that compounds of this first preferred group generally have good activity against whitefly and, when the longest 3 position chain is 7 carbons or less, fungi, eg. *R. solani*, *P. oryzae* and *A. niger*, while retaining activity against mites.

In a second preferred distinct group of compounds provided for the use of the first aspect of the invention the moiety —CH$R^4R^5$ is provided as part of a cycloalkyl or cycloalkenyl ring and thus this second group of preferred compounds of formula (I) are of preferred formula (III)

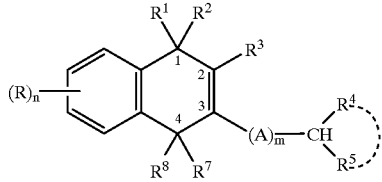

(III)

wherein
n, A, R, $R^1$, $R^2$, $R^3$, $R^7$ and $R^8$ are as defined for general formula (I);
m represents an integer 0 to 1;
and $R^4$ and $R^5$ together with the interjacent carbon atom represent an optionally substituted $C_{5-7}$ cycloalkyl or cycloalkenyl ring.

More preferably the compounds of this group are of formula (III) wherein $R^1$ with $R^2$, and $R^7$ with $R^8$ are both =O; n and m are 0; and $R^4$ and $R^5$ together with the interjacent carbon atom represent a fully saturated $C_{5-7}$ cycloalkyl ring which is optionally substituted.

Still more preferably $R^4$ and $R^5$ together with the interjacent carbon atom represent a $C_{5-7}$ saturated cycloalkyl ring substituted with halogen, most preferably chlorine or fluorine, or with $C_{1-4}$ alkyl or haloalkyl or $C_{2-4}$ alkenyl or haloalkenyl group $R^{20}$. Most preferably $R^4$ and $R^5$ together with the interjacent carbon atom represent a cyclopentyl or cyclohexyl ring substituted in one or more of the 2, 3 or 4 positions with a group $R^{20}$.

Preferred compounds of this second preferred group of the invention are exceptionally effective against whitefly, especially species of *B. tabaci*, when the cycloalkyl or cycloalkenyl ring is directly attached to the naphthalene ring, ie. m=0.

In a third distinct group of compounds of the first aspect of the invention the moiety —CH$R^4R^5$ does not represent a cycloalkyl or cycloalkenyl ring and is provided spaced by between 1 and 6 carbon atoms length away from the naphthalene ring, and most preferably between 2 and 4 carbon atoms length away from the naphthalene ring.

Thus in this distinct group of compounds for the use of the invention the compounds of formula (I) are of preferred formula (IV)

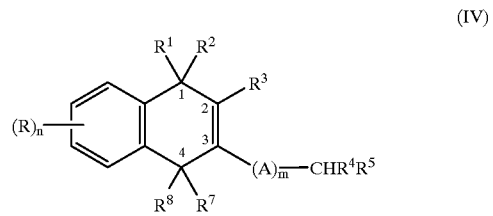

(IV)

wherein
n, A, R, $R^1$, $R^2$, $R^3$, $R^7$ and $R^8$ are as defined for general formula (I); and
$R^4$ and $R^5$ each independently represent a halogen or optionally substituted alkyl or alkenyl group.

More preferred compounds of this group are of formula (IV) wherein n is 0, $R_1$ with $R^2$, and $R^7$ with $R^8$ are both =O; A is a $C_{1-6}$ alkyl, $C_{1-6}$ haloalkyl, $C_{2-6}$ alkenyl or $C_{2-6}$ haloalkenyl chain, which may be substituted by a halogen or a branch chain which may be halogenated. Preferably $R^4$ and $R^5$ are $C_{2-6}$ alkyl or haloalkyl or $C_{2-6}$ alkenyl or haloalkenyl.

$R^3$ is preferably —OH, —O—CO—$R^{11}$ or —O—CO—O—$R^{11}$ where $R^{11}$ is $C_{1-3}$ alkyl, and most preferably OH.

Preferred compounds of this group are those where A is a group —$(CH_2)_a$—where a is an integer of 1 to 6, more preferably 1 to 4, or —$(CH_2)_a$—CH=CH—$(CH_2)_b$—where a and b are integers which add up to 0 to 4, and analogues of these wherein one or more of the carbon atoms in the these groups are substituted by alkyl, haloalkyl, alkenyl, haloalkenyl or halogen.

Particularly effective compounds of formula (III) for the use of the invention are those wherein one or more of A, $R^4$ and $R^5$ includes a haloalkyl or haloalkenyl group, particularly a trifluoromethyl group. Preferred compounds include those where —A—$CHR^4R^5$ is an isofluoroalkyl group, eg. such as 2-trifluoromethylpropyl or 2,2-di-trifluoromethylethyl. Both unsubstituted and halogenated compounds have good activity against the aforesaid fungi when the longest chain at the 3 position is up to 7 carbons.

A second aspect of the present invention provides novel compounds of formula (I), wherein —$CHR^4R^5$ forms a 2-substituted cycloalkyl ring, preferably 2-substituted by $C_{1-4}$ alkyl or $C_{1-4}$ haloalkyl; or —$(A)_m$—$CHR^4R^5$ is an isohaloalkyl group.

Preferred 2-substituted cycloalkyl compounds, such as 2-hydroxy-3-(2-methyl-cyclohexyl)-naphthalene-1,4-dione, are not only novel, but have surprisingly high activity against whitefly as compared to the 3- and 4- substituted cycloalkyl compounds.

Thus this aspect of the invention particularly provides a compound of formula (VI)

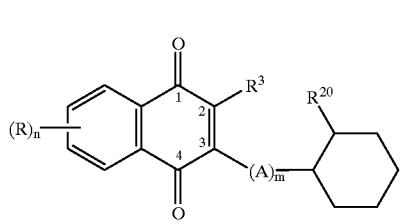

(VI)

wherein n, m, A, R, $R^1$, $R^2$, $R^3$, $R^7$ and $R^8$ are as defined for general formula (I) and $R^{20}$ is selected from $C_{1-4}$ alkyl, $C_{1-4}$ haloalkyl, $C_{2-4}$ alkyl and $C_{2-4}$ haloalkyl.

This aspect of the invention further particularly provides a compound of formula (VII)

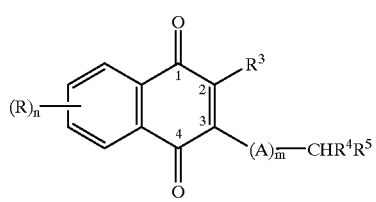

(VII)

wherein n, m, A, R, $R^1$, $R^2$, $R^3$, $R^7$ and $R^8$ are as defined for general formula (I) and one or more of A, $R^4$ and $R^5$ is or includes a haloalkyl group. Preferred such compounds have A as a $C_{1-4}$ alkylene group and one or both of $R^4$ and $R^5$ is trifluoromethyl.

Preferred isohaloalkyl compounds of formula (VI), such as 2-hydroxy-3-(2-trifluoromethylpropyl)-naphthalene-1,4-dione, are not only novel, but have high activity against mites as well as whitefly.

Further novel compounds of the invention are those of formula (I) where $R^1$ with $R^2$ and/or $R^7$ with $R^8$ are not both =O.

A third aspect of the present invention provides a method of combatting whitefly, Lepidoptera and/or fungal pests at a locus which comprises treating the locus with a compound of the general formula (I), preferably of general formula (II), (III) or (IV).

Preferably, the locus comprises the pests, i.e. whitefly, Lepidoptera and/or fungi, per se or environments subject to or subjected to attack by pests. More preferably, the locus comprises the pests per se, stored food material, plants or animals subject to or subjected to attack by pests, seeds of such plants or the medium in which such plants are growing or are to be grown. Specifically, compounds of formula I may be used in a domestic environment for spraying rooms to combat infestation by houseflies or other insects, acarids or fungi, in a horticultural or agricultural environment for treatment of stored crops, especially cereals, or to spray growing crops such as cotton or rice to combat infestation by pests, particularly whitefly and related species, and in a medical or veterinary environment, for instance, as a cattle spray to prevent or treat infestation the pests.

In a fourth aspect the present invention also provides processes for the preparation of compounds of formula (I) and particularly of formula (II), (III) and (IV) as defined above.

In a preferred process for preparing compounds of formula (I), (II), (III) and (IV), a compound of the general formula (V)

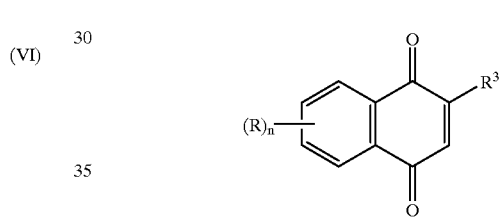

(V)

in which n, R and $R^3$ are as defined above, is reacted with a carboxylic acid $CHR^4R^5$—$(A)_m$—COOH where $R^4$ and $R^5$ are as defined above, in the presence of a free radical initiator, such as ammonium peroxysulphate and silver nitrate in a suitable solvent, such as aqueous acetonitrile, to form a compound of the general formula (I), (II), (III) or (IV). Compounds of formula (V) are commercially available but in any case may be prepared from corresponding available benzoquinones and substituted alkenes using eg. Diels Alder conditions.

In a still further process for preparation of the compounds of the present invention the compound of formula (V) is reacted with a compound of formula X—$(A)_m$—$CHR^4R^5$ wherein $R^4$, $R^5$, A and m are as defined for formula I and X is a leaving group that will leave the compound to give a charged radical $^+(A)_m$—$CHR^4R^5$; eg. X may be a halogen atom or tosyl group. This reaction is carried out in the presence of an acid, eg. a Lewis acid such as aluminium chloride, using conditions broadly as described by Fieser and Gates (J. Am. Chem. Soc. (1941) 63, 2943–2953.

Compounds of formula (I) obtained by these processes may then be further reacted using the derivatisation processes described above or combinations thereof to obtain further compounds of formula (I), as desired.

For use in this alternative method, in the case where $R^4$ and $R^5$ together with their interjacent carbon atom form a cycloalkyl or cycloalkenyl ring of from 3 to 10 carbons, many of the cycloalkyl and cycloalkylenecarboxylic acids are commercially available and the carboxylic acid groups thereon may be extended by known techniques to give access to longer carbon chain lengths, and then substituted if required using techniques well known to those skilled in the art. For example the Arnst-Elstert reaction may be used to give a —CH$_2$— extension (see e.g. Meier and Zeller (1975) *Angew. Chem. Int. Ed. Ewgl.*, 14, 32). Alternatively compounds where m is 1 may be accessed by the reaction of the corresponding cycloalkanone with ethyl cyanoacetate and subsequent reaction with a Grignard reagent, followed by hydrolysis to yield the cycloalkyl acetic acid (see e.g. Amsterdamsky et al (1975) Bull. Soc. Chim. Fr. (3–4 Part 2), p635–643 and Muhs M. A. PhD Thesis, University of Washington, Diss Abst. 14, 765 (1954) to increase the carbon chain length in increments of 1.

For preparation of compounds containing $R^4$ $R^5$ rings having higher numbers of carbons, the corresponding monobromo-substituted cycloalkyl or cycloalkenyl compounds may be converted to the carboxylates by formation of the Grignard compound using magnesium and then treating this with $CO_2$, e.g. in the form of dry ice. The carboxylic acid so formed may be converted to the alkyl carboxylate by alkylation using, e.g. a compound $R^6$-I, e.g. methyl iodide, in the presence of butyl-lithium, where $R^6$ is a group as defined above that is stable under these conditions.

Substitutions, e.g. alkylation, of the cycloalkyl/ cycloalkylene ring at positions other than the 1-position to the carboxylate may be accomplished by methods known to those skilled in the art. Starting from the ring mono-unsaturated cycloalkylene carboxylic alkyl esters, alkylation may be directed at the desired position as previously described and then, using light as initiator, reaction with e.g. $CF_3X$ allows introduction of $CF_3$-groups with reduction using palladium carbon catalysis conditions allowing saturation of the unsaturated bond. Many other manipulations will occur to those skilled in the art for the purposes of accessing other compounds of the general formula (I).

Compounds of formula (I) in which $R^3$ represents a leaving group as defined above may be prepared by reacting a compound of formula (I) in which $R^3$ represents a hydroxyl group with a compound X-L, where X represents a halogen atom, in the presence of an organic base, preferably a tertiary amine such as triethylamine, or an inorganic base such as sodium carbonate. For instance compounds of formula I in which $R^3$ represents a group —O—CO—$R^{11}$, where $R^{11}$ is as defined above, may be prepared by acylation of the hydroxy group in a suitable compound of formula I for instance, by using an acyl chloride $R^{11}$—CO—Cl in a suitable solvent, such as dichloromethane, in the presence of a base, such as triethylamine. Alternatively compounds of formula I in which $R^3$ represents a hydroxyl group may be reacted with a compound HO-L where L is as defined above and includes the acid C=O, in the presence of a dehydrating agent such as dicyclohexylcarbodiimide. A further route to such compounds is provided by reacting a metal salt of a compound of formula (I) in which $R^3$ represents a hydroxyl group, that is, $R^3$ represents a group —OM where M is a metal ion, with a compound X-L as defined above.

Compounds of formula (I) in which $R^1$ with $R^2$ and/or $R^7$ with $R^8$ each independently represent an optionally substituted alkoxy group may be prepared by ketalisation of one or both carbonyl groups in a suitable compound of formula (I) or (V), for instance, by using a suitable alcohol in basic or acidic conditions, such as by use of a solution of potassium hydroxide in methanol.

Compounds of formula (I) in which $R^1$ with $R^2$ together and/or $R^7$ with $R^8$ together represent a thiocarbonyl group =S may be prepared by treating a suitable compound of formula (I), wherein $R^1$ with $R^2$ and $R^7$ with $R^8$ are both =O, with a thiating agent, such as Lawesson's Reagent (2,4-bis(4-methoxyphenyl)-1,3-dithia-2,4-diphosphetane-2, 4-disulphide), using protecting groups where required.

Compounds of formula (I) in which $R^1$ and $R^2$ together and/or $R^7$ and $R^8$ together represent an oxime group =N—$OR^9$, where $R^9$ is as defined above, may be prepared by treating a suitable compound of formula (I), wherein $R^1$ and $R^2$ and $R^7$ and $R^8$ are both =O, with a hydroxylamine or alkoxylamine of formula $R^9O$—$NH_2$, where $R^9$ is as defined above, in the presence of a base, such as pyridine.

Combinations of the above derivatisation processes may be performed to achieve the desired compound of formula (I).

In a fifth aspect of the present invention an insecticidal and/or fungicidal composition is provided which comprises a compound of formula (I) and preferably of formula (II), (III) or (IV), as defined above, in association with at least one carrier. Such a composition may contain a single compound or a mixture of several compounds of the present invention. It is also envisaged that different isomers or mixtures of isomers may have different levels or spectra of activity and thus compositions may comprise individual isomers or mixture of isomers.

The compositions of the invention typically contain from 0.001 to 95% by weight of the active ingredient of formula I. Preferably the compositions contain from 0.001 to 25% by weight of the active ingredient when they are in ready-to-use form. However, higher concentrations, for instance, up to 95%, may be present in compositions to be sold as concentrates for dilution before use.

The compositions of the invention may be mixed with a variety of appropriate inert carriers such as solvents, diluents and/or surface-active agents to form dusts, granular solids, wettable powders, mosquito coils or other solid preparations or emulsions, emulsifiable concentrates, sprays, aerosols or other liquid preparations. Suitable solvents and diluents include water, aliphatic and aromatic hydrocarbons such as xylene or other petroleum fractions and alcohols such as ethanol. Surface-active agents may be of an anionic, cationic or non-ionic type. Anti-oxidants or other stabilisers may also be included as well as perfumes and colourings. These inert carriers may be of the type and in proportions such as are conventionally used in pesticidal compositions. These inert carriers may be of the type and in proportions such as are conventionally used in pesticidal compositions and thus are conveniently inert with respect to the physiology of a plant to be treated.

Examples of carriers known to be suitable for use in compositions incorporating naphthalene-1,4-diones for pesticidal use include those described in the specifications, and more specifically the Examples, of U.S. Pat. Nos. 2,572,946, 4,110,473, 4,970,328 and JP 90/152943 (the latter to Agro-Kanesho KK).

In addition to these inert carriers, the compositions of the invention may also contain one or more further active ingredients. These further active ingredients may be other compounds which exhibit pesticida synergistic effect with the compounds may exhibit a synergistic effect with the compounds of the present invention.

The present invention will now be described further by way of illustration only by reference to the following non-limiting Examples and Comparative Examples. Further embodiments of the invention will occur to those skilled in the art in the light of these.

EXAMPLES

Example 1
Preparation of 2-cyclohexyl-3-hydroxy-naphthalene-1.4-dione

To a stirred solution of 2-hydroxynaphthalene-1,4-dione (1.00 g, 5.74 mmol), cyclohexane carboxylic acid (1.10 g, 8.61 rnmol) and silver nitrate (520 mg) in acetonitrile (15 ml) and water (20 ml) heated at 65–70° C. was added an aqueous solution of ammonium persulphate (1.77 g, 7.77 mmol) in water (10 ml). After heating for 1 hour the mixture was cooled, diluted with water (50 ml) and extracted with ether (3×40 ml). The combined ether fractions were washed with water (3×25ml), saturated sodium chloride solution (25 ml) and dried over magnesium sulphate. Filtration and evaporation of solvents under reduced pressure and silica gel chromatography yielded the title compound (364 mg, m.p. 133° C.). This compound is listed as compound 12 in the Tables below.

Example 2
Preparation of 2-hydroxy-3-(4-methylcyclohexyl)-naphthalene-1.4-dione The method of Example 1 was followed using lawsone, ie. (2-hydroxynaphthalene- 1,4-dione (1.00 g), and 4-methylcyclohexanecarboxylic acid (1.23 g), and yielded the title compound (100 mg, m.p. 101° C.).

This compound is listed as compound 19 in the Tables below.

Example 3
Preparation of 2-hydroxy-3-(1-methylbutyl)-naphthalene-1,4-dione

The method of Example 1 was followed using 2-acetyloxynaphthalene-1,4-dione (1.24 g, 5.74 mmol) and 2-methylpentanoic acid (1.00 g) yielded the title compound (608 mg) after hydrolysis in. 30 ml THF using potassium hydroxide (5×exess) in water (8 ml) (mp 82–83° C.). This compound is listed as compound 3 in the Tables below.

Example 4
Preparation of 2-hydroxy-3-(2-trifluoromethylpropyl)-1,4-naphthoquinone 2-acetyloxynaphthalene-1,4-dione (1.24 g) and 3-trifluoromethylbutanoic acid (1.08 g) were reacted using the method as descibed in Example 3 yielding the title compound (353 mg) (mp 168° C.). This compound is listed as compound 11 in the Tables below.

Other compounds set out in the tables below were produced using these general methods. Example 20 is Example 1 of Table 1 of DE 3801743 Al which is 2-hydroxy-3-(4-t-butylcyclohexyl)naphthalene-1,4-dione (Formula I: n=0; m=0, $R^1+R^2$ together and $R^7+R^8$ together both represent =O; $R^3$=—OH; —$CHR^4R^5$—=4-t-butylcyclohexyl).

TABLE 1

(in all the following examples n = O and $R^7$ and $R^8$ together represent a group = O)

| Compound No. | $R^1$ | $R^2$ | $R^3$ | A | —$CHR^4$ $R^5$— | M. pt (° C.) |
|---|---|---|---|---|---|---|
| 1 | =O | —OH | —$CH_2$— | —$CH(C_2H_5)_2$ | 110–111 |
| 2 | " | " | — | —$CHCH_3CH=CH_2$ | 58–61 |
| 3 | " | " | — | —$CH(CH_3)C_2H_5$ | 82–83 |
| 4 | " | " | —$(CH_2)_2$— | —$CH(CH_3)_2$ | 82–83 |
| 5 | " | " | — | —$CH(CH_3)$—$CH_3$ | 90 |
| 6 | " | " | — | —$CH(CH_3)CH_2\;COCH_3$ | 106 |
| 7 | " | " | —$(CH_2)_3$— | —$CH_3$ | 121–3 |
| 8 | " | " | —$(CH_2)_4$— | —$CH_3$ | 103–4 |
| 9 | " | " | —$(CH_2)_5$— | —$CH_3$ | 75–6 |
| 10 | " | " | —$(CH_2)_7$— | —$CH_3$ | 81–2 |
| 11 | " | " | —$CH_2$— | —$CH(CH_3)CF_3$ | 168 |

NB $^nD$ signifies refractive index for the sodium D lines;
'—' indicates absence of a group A

TABLE 2

In all the following examples n = 0, $R^1$ + $R^2$ together and $R^7$ + $R^8$ together both represent =O; $R^3$ = OH and m = 0.

| Compound No. | —$CHR^4R^5$— | M. pt (° C.) |
|---|---|---|
| 12 | cyclohexyl | 133 |
| 13 | cyclopentyl | 98–99 |
| 14 | cyclobutyl | 125–127 |
| 15 | cycloheptyl | 94–95 |
| 16* | cyclopropyl | 86–87 |
| 17 | 2methylcyclohexyl | 89–90 |
| 18 | 3methylcyclohexyl | 104–5 |
| 19 | 4methylcyclohexyl | 101–2 |
| 20 | 4t-butylcyclohexyl | 96–97 |

*Comparative Example = Compound No 16.

Pesticidal Activity

Pesticidal activity was assessed against houseflies, mustard beetles, mites and whitefly using the following methods.

Houseflies (MD) (*Musca domestica*)

Female flies were treated on the thorax with a one microlitre drop of test compound dissolved in acetone. Two replicates of 15 flies were used at each dose rate and 6 dose rates were used per compound under test. After treatment, the flies were maintained at a temperature of 20°±1° C. and kill was assessed 24 and 48 hours after treatment. $LD_{50}$ values were calculated in micrograms of test compound per fly (see Sawicki et al., *Bulletin of the World Health Organisation,* 35, 893 (1966) and Sawicki et al., *Entomologia and Exp. Appli* 10, 253, (1967).

Mustard beetles (PC) (*Phaedon cochleariae* Fab)

A one microlitre drop of an acetone solution of the test compound was applied ventrally to adult mustard beetles using a micro drop applicator. The treated insects were maintained for 48 hours after which time kill was assessed. Two replicates each of 20 to 25 mustard beetles were used at each dose level and 5 dose levels were treated comparably. $LD_{50}$ values were calculated as for houseflies.

Mites (TU) (*Tetranychus urticae*)

25 adult female mites were immersed in 35 µl of a solution of the test compound in a 1:4 acetone-water mixture for 30 seconds. The treated insects were maintained at 21°±2° C. and kill was assessed 72 hours after treatment. Mites exhibiting repetitive (non-reflex) movement of more than one locomotory appendage after this period were recorded as alive. Three replicates of 25 mites each were used at each dose rate and 5 or 6 dose rates were used per compound under test. $LC_{50}$ values were calculated in ppm of the solution of the test compound per insect. The test was carried out using a susceptible strain of mites (GSS) supplied by Schering, AG, Berlin.

Whitefly (BT) (*Bemisia tabaci*)

Acetone solutions (0.100 ml) of the test compounds were placed in 10 ml glass vials and evaporated with rotation to deposit a film of the compound. Thirty adult whiteflies were placed inside the vial, then after 60 minutes, the treated insects were transferred onto untreated cotton leaf discs which were kept moist on a bed of agar gel. The temperature was maintained at 25° C. and mortality assessed after 48 hours. Three replicates were used at each of 5 to 7 dose levels per compound. $LC_{50}$ values were calculated by using a computer software package ("Polo-PC available from LeOra Software, Berkeley, Calif.). (See M. R. Cahill and B. Hackett in Proceedings Brighton Crop Protection Conference, 1992). The test was carried out using a susceptible strain of whitefly (SUD-S) which was collected in Sudan in 1978 from cotton.

The results of these tests are set out in Tables 3 and 4 below. The values given are $LD_{50}$ (µg/insect) or $LC_{50}$ (ppm solution of test compound) unless otherwise specified.

TABLE 3

| Compound No. | MD ($LD_{50}$) | PC ($LD_{50}$) | PX ($LD_{50}$) | TU(GSS) ($LC_{50}$) | BT(SUD-S) ($LC_{50}$) |
|---|---|---|---|---|---|
| 1 | c. 2.5 | 3.0 | — | 29 | 19 |
| 2 | 1.6 | 1.9 | — | 82 | 18 |
| 3 | c. 1.5 | c. 4.0 | — | c. 500 | 12 |
| 4 | c. 3.5 | c. 0.8 | — | 80 | 23 |
| 5 | 2.8 | 5.8 | — | c. 500 | 10 |
| 6 | — | >20 | — | — | — |
| 7 | c10 | c5 | — | 65 | 13 |
| 8 | NA | c7 | — | 16 | 17 |
| 9 | c20 | c7 | NA | 170 | 9.4 |
| 10 | 1.9 | 0.78 | — | c1000 | 19 |
| 11 | NA | 12 | — | 8 | 4.8 |
| A | >>20 | 0.36 | — | 64 | 82 |

Compound A = Example 1, page 5 of DE 2641343 A1 which is 2-n-dodecyl-3-ethanoyloxynaphtahlene-1,4-dione (Formula I: n = 0; m = 1; $R^1 + R^2$ together and $R^7 + R^8$ together are both = 0; $R^3$ = —0-CO—$CH_3$; A = —$CH_2$—; —$CR^4R^5$— = —$^nC_{11}H_{23}$)

TABLE 4

| Compound No. | MD ($LD_{50}$) | PC ($LD_{50}$) | TU(GSS) ($LC_{50}$) | BT(SUD-S) ($LC_{50}$) |
|---|---|---|---|---|
| 12 | <20 | <2 | c. 50 | 6.8 |
| 13 | 2.5 | <2 | 40 | 6.1 |
| 14 | >10 | c. 10.0 | 150 | 25 |
| 15 | 2.6 | 0.9 | 37 | 3.0 |

TABLE 4-continued

| Compound No. | MD ($LD_{50}$) | PC ($LD_{50}$) | TU(GSS) ($LC_{50}$) | BT(SUD-S) ($LC_{50}$) |
|---|---|---|---|---|
| 16* | >10 | >10 | c. 500 | c. 50 |
| 17 | 1.2 | 0.53 | 12 | 1.1 |
| 18 | 1.5 | 0.86 | 7.4 | 3.9 |
| 19 | 2.0 | c 1 | 7.3 | 4.5 |
| 20 | 15.5 | 0.53 | 44 | 18 |

*Compound 16 = Comparative Example

Activity Against Resistant Whitefly (BT) (*Bemisia tabaci*)

The whitefly test on (BT (SUD-S)) was repeated using a resistant strain of whitefly (Ned ½). The Ned ½ strain is a composite collection which was collected in the Netherlands in 1992 from Gerbera and Bouvardia by ICI Netherlands and exhibits high resistance to pyrethroid insecticides, such as cypermethrin, organophosphate and carbamate insecticides and the insect growth regulator buprofezin. The result of this test is set out in Table 5 below. The value given ise $LC_{50}$ (pPm solution of test compound).

TABLE 5

| Compound No. | BT (Ned ½) ($LC_{50}$) |
|---|---|
| 12 | 6.4 |
| 20 | 100 |

In addition to activity against whitefly, the presently investigated compounds were also found to have activity against Diabrotica (Western Corn Root worm), and Lepidoptera, eg. Spodoptera eg. *S. littoralis* and *S. frugiperda*. For example Compound 4 has $LC_{50}$ ppm topical of the order of 5, 10 and 20 for these three species, while Compound 13 has $LC_{50}$ values of approximately 20, 12 and 20 respectively; Diabrotica, *S. littoralis* and *S. frugiperda*. Antifeedant activity is also evident in the species specified.

Fungicidal Activity

Fungitoxicity of coded compounds to isolates of *Aspergillus niger*, *Pyricularia oryzae* (=*Magnaporthe grisea*) and *Rhizoctonia solani* was tested in vitro.

Each compound was incorporated into potato dextrose agar in solvent (50/50 ethanol/acetone) at 0.5 ml solvent per 250 ml agar while the autoclaved agar was still molten and cooled to 50° C. Each compound was tested at a single concentration (100 mg $l^{-1}$).

Each test, usually of two compounds, included three control treatments: a standard fungicide (carbendazim at 1 or 5 mg $l^{-1}$ or prochloraz at 1 mg $l^{-1}$); ethanol/acetone only; no additions. The fungicides used as standards may be considered as representative of active commercially available compounds.

Each fungus was tested on agar in four Petri dishes per treatment, with three replicate fungal colonies per plate (one colony for *R. solani*). *A. niger* and *R. solani* were incubated for 4 days at 20–25° C., and *P. oryzae* for 7 days. Increase in colony diameter was then measured and used to determine activity:

The results of these tests are set out in Table 6 below. The values given are % inhibition of growth in colony diameter in agar plates at a given concentration of agent.

Compound numbers are as above with the addition of compound number 21: -2-methyl-3-hydroxynaphthalene-1,4-dione, and compound number 22: -2-ethyl-3-hydroxynaphthalene-1,4-dione. Inhibition by standard agents is given for comparison.

TABLE 6

| Compound of Example No. | Fungus | Activity at 1% | Activity at 0.2% | Activity at 0.1% |
|---|---|---|---|---|
| 3 | A. niger | 77 | 42 | |
| 11 | A. niger | 50 | 36 | |
| 21 | A. niger | 100 | 76 | |
| 22 | A. niger | 100 | 100 | 57 |
| 3 | P. oryzae | 100 | — | |
| 11 | P. oryzae | 100 | 100 | |
| 21 | P. oryzae | 100 | 100 | 23 |
| 22 | P. oryzae | 100 | 100 | 89 |
| 3 | R. solani | 100 | 89 | |
| 11 | R. solani | 67 | 56 | |
| 21 | R. solani | 100 | 63 | 41 |
| 22 | R. solani | 100 | 87 | 64 |
| Prochloraz | A. niger | | | 97.8 |
| Carbendazim | P. oryzae | | 99.8 | 14.7 |
| Carbendazim | R. solani | | 82.4 | 3.3 |

In addition, tests have shown that the compounds of formula I exhibit good fungicidal activity against a broad spectrum of fungi which cause diseases in both cereal and broad leaved crops. Particularly, good activity has been observed against fungi of the genera Erysiphe, especially *Erysiphe graminis,* and Botrytis, especially *Botrytis fabae* and *Botrytis cinerea,* as well as the genera Rhizoctonia, Pyricularia and Aspergillus as illustrated above.

TABLE 6

Insecticidal and acaricidal activity of comparative examples and Examples 21 and 22(*); $R^1R^2$ and $R^7R^8 = =O$; $R^3 = OH$; n and m = 0

| Naphthalene 3 position | PC $LD_{50}(\mu g/insect)$ | MD $LD_{50}(\mu g/insect)$ | MP % kill 100 ppm | TU $LC_{50}(ppm/insect)$ | BT $LC_{50}(ppm/insect)$ |
|---|---|---|---|---|---|
| 5 —H | NA | NA | — | NA | NA |
| —CH3* | NA | NA | — | NA | NA |
| —CH$_2$CH3* | NA | NA | — | NA | NA |
| —(CH$_2$)$_9$CH$_3$ | 1.9 | NA | — | 5.5 | >100 |
| —(CH$_2$)$_{10}$CH$_3$ | c0.4 | NA | — | 1.4 | >100 |
| 10-(CH$_2$)$_{11}$CH$_3$ | NA | NA | — | <60 | >100 |
| —(CH$_2$)$_{13}$CH$_3$ | NA | NA | — | 1.3 | NA |

Example 5
Preparation of 2-hydroxy-naphthalene-1 4-dione Starting Materials for Compounds where n=1 or more Diels-Alder type reactions using corresponding quinone compounds yield suitable starting material 2-hydroxy-naphthalene-1,4-diones for preparation of compounds where n=1 or more. Examples are as follows.

(a) Preparation of 6-methyl-naphthalene-1,4-dione

A solution of 1,4-benzoquinone (13.9 g, 128 mmol) and isoprene (13.1 ml, 131 mmol) was stirred in glacial acetic acid (44 ml) for 68 hours at room temperature. The mixture was diluted with water (44 ml) and refluxed for 1½ hours. The mixture was cooled to room temperature and acetic acid (84 ml) and chromic acid [chromium trioxide (29.4 g)] in water (30 ml)] was added sequentially, before refluxing for a further 1½ hours. After cooling, the mixture was diluted with water (200 ml) and extracted with ether (3×50 ml). The combined ether fractions were washed with dilute sodium hydroxide solution (2M; 2×50 ml), water (2×50 ml), saturated sodium chloride solution (50 ml) and dried over magnesium sulphate. Filtration and evaporation of solvent under reduced pressure, and repeated recrystallisation from petroleum ether yielded the title compound (7 g).

(b) 2-Amino-6 and 7-methyl-1,4-naphthalene-1.4-diones

To a stirred solution of 6-methyl naphthalene-1,4-dione (2.1 g, 12 mmol) in glacial acetic acid (60 ml) at room temperature was added a solution of sodium azide (1.58 g) in water (5 ml). The mixture was stirred for 2 days before diluting with water (200 ml) and, after stirring for a further 15 minutes, was filtered. The filtrate was neutralised with sodium bicarbonate and extracted with chloroform (3×25 ml). The combined chloroform extracts were washed with saturated sodium bicarbonate solution, brine and dried (CaSO$_4$). Filtration and evaporation of solvent under reduced pressure and silica gel chromatography yielded the title compound (100 mg) as a 3:2 mixture of isomers.

(c) 2-Hydroxy-6- and -7-methylnaphthalene-1.4-diones

The aminomethyl naphthalene-1,4-dione mixture from (b)(200 mg) was refluxed in water (20 ml) and concentrated sulphuric acid (10 ml) for 20 minutes. The cooled mixture was poured into ice/water (50 g) and extracted with ether (3×25 ml). The combined ether extracts were washed with water, saturated NaHCO$_3$, water, saturated NaCl solution and dried (MgSO$_4$). Filtration and evaporation of solvent and purification by silica gel column chromatography yielded the title compound (68 mg).

We claim:

1. A method of combating white fly or Lepidoptera pests at a locus, which comprises treating the locus with a compound of formula (I)

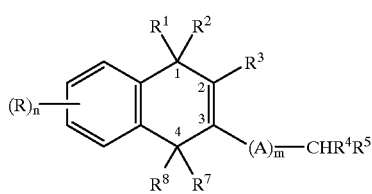

or a salt thereof, in which n represents an integer from 0 to 4; m represents an integer 0 or 1;

each R independently represents a halogen atom or a nitro, cyano, hydroxyl, alkyl, alkenyl, haloalkyl, haloalkenyl, alkoxy, haloalkoxy, haloalkenoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl, aryl or aralkyl group; $R^1$ and $R^2$ each independently represent an optionally substituted alkoxy group or together represent a group $=O$, $=S$ or $=N$—$OR^9$, where $R^9$ a hydrogen atom or an optionally substituted alkyl group;

$R^3$ represents a hydroxyl group, or a group —OL where L is a leaving group, or a group which in vivo is transformed into a group —$OL^1$ is a leaving group;

R[7] and R[8] independently represent an optionally substituted alkoxy group or together represent a group =O, =S or =N—OR[9], where R[9] is as previously defined;

wherein $R_4$ and $R_5$ independently represent a hydrogen or halogen atom or an optionally substituted alkyl or alkenyl group, or together with the interjacent carbon atom represent an optionally substituted $C_{4-8}$ cycloalkyl or cycloalkenyl ring; and A represents a straight or branched chain alkyl or alkenyl group, which may be optionally substituted, an acyclic carbon chain of which links the 3 position of the naphthalene ring shown and the moiety —CHR[4]R[5] and wherein A does not include a quaternary carbon atom in that chain; and wherein the total number of carbon atoms in the longest carbon chain running from the 3-position of the naphthalene ring shown is no more than 8.

2. A method as claimed in claim 1, wherein the pest is Bemisia whitefly.

3. A method as claimed in claim 2, wherein the pest is *Bemisia tabaci*.

4. A method as claimed in claim 1, wherein the pest is Spodoptera.

5. A method as claimed in claim 1, wherein the locus comprises the pest per se or environments subject to or subjected to attack by the pests.

6. A method as claimed in claim 1, wherein R[1] with R[2], and R[7] with R[8] each independently represent a $C_{1-4}$ alkoxy group or R[1] with R[2] and/or R[7] with R[8] together represent a group =O.

7. A method as claimed in claim 1, wherein R[3] is a group —OL where L is a leaving group, or a group which in vivo is transformed into a group —OL[1], wherein the $pK_a$ value of the acid LOH or L[1]OH in water is from 1 to 7.

8. A method as claimed in claim 6, wherein R[3] is a group which in vivo is transformed into a group —OL[1] where L[1] is a leaving group and the transformation is carried out in a pest to be combated.

9. A method as claimed in claim 1, wherein the compound of formula (I) is a naphthalene-1,4-dione.

10. A method as claimed in claim 1, wherein R[4] and R[5] independently represent a $C_{1-4}$ alkyl or haloalkyl group or a $C_{2-4}$ alkenyl or haloalkenyl group, or together with the interjacent carbon atom, represents a $C_{4-8}$ cycloalkyl or cycloalkenyl ring which is optionally substituted with one or more substituents independently selected from halogen atoms and $C_{1-4}$ alkyl, $C_{1-4}$ haloalkyl, $C_{2-4}$ alkenyl and $C_{2-4}$ haloalkenyl groups.

11. A method as claimed in claim 1 wherein the compound is of formula (II)

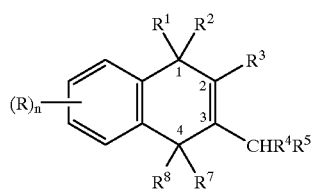

(II)

or a salt thereof in which R, R[1], R[2], R[3], R[7], and R[8] and n are as defined in formula I and R[4] and R[5] each independently represent a halogen or an optionally substituted alkyl or alkenyl group.

12. A method as claimed in claim 11, wherein n is 0; R[1] with R[2], and R[7] with R[8] are both =O; R[4] and R[5] each independently represent a $C_{1-4}$ alkyl, $C_{1-4}$ haloalkyl, $C_{2-4}$ alkenyl or $C_{2-4}$ haloalkyl group.

13. A method as claimed in claim 11, wherein —CHR[4]R[5] represents a methyl or ethyl group.

14. A method as claimed in claim 1, wherein the compound is of formula (III)

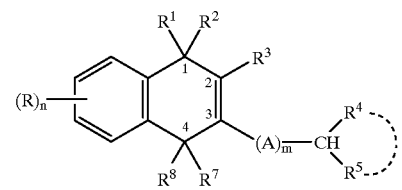

(III)

wherein n, m, A, R, R[1], R[2], R[3], R[7] and R[8] are as defined for formula (I);

and R[4] and R[5] together with the interjacent carbon atom represent an optionally substituted $C_{4-8}$ cycloalkyl or cycloalkenyl ring.

15. A method as claimed in claim 14, wherein R[1] with R[2], and R[7] with R[8] are both =O; n and m are 0; and R[4] and R[5] together with the interjacent carbon atom represents a fully saturated $C_{4-8}$ cycloalkyl ring which is optionally substituted.

16. A method as claimed in claim 11, wherein the compound is of formula (IV)

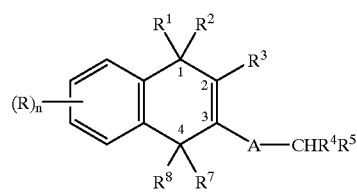

(IV)

or a salt thereof wherein n, A, R, R[1], R[2], R[3], R[7], and R[8] are as defined for formula (I); and R[4] and R[5] each independently represent a halogen or optionally substituted alkyl or alkenyl group.

17. A method as claimed in claim 16, wherein R[1] with R[2], and R[7] with R[8] are both =O; m is 1 and A is a $C_{1-6}$ alkyl or $C_{2-6}$ alkenyl chain, which may be substituted by halogen or a branch alkyl or alkenyl chain which may be halogenated.

18. A method as claimed in claim 16, wherein R[4] and R[5] are independently selected from the group consisting of $C_{1-6}$ alkyl, $C_{1-6}$ haloalkyl, $C_{2-6}$ alkenyl and $C_{2-6}$ haloalkenyl.

19. A method as claimed in claim 16, wherein A is group —(CH$_2$)$_a$— wherein a is an integer from 1 to 6 or —(CH$_2$)$_a$—CH=CH—(CH$_2$)$_b$— where a and b are integers which add up to 0 to 4, or an analogue of these wherein one or more of the carbon atoms in these groups are substituted by alkyl, haloalkyl, alkenyl, haloalkenyl or halogen.

20. A method as claimed in claim 19, wherein a is an integer from 1 to 4 or a and b are integers which add up to 0 to 2.

21. A compound of formula (VI)

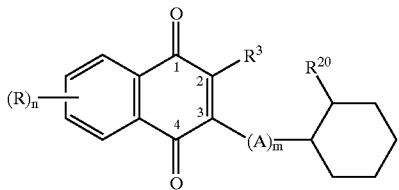

(VI)

wherein m, n, A, R and $R^3$ are as defined for formula (I) in claim 1 and $R^{20}$ is selected from the group consisting of $C_{1-4}$ alkyl, $C_{2-4}$ alkenyl and $C_{2-4}$ haloalkenyl.

22. A compound of formula (VII)

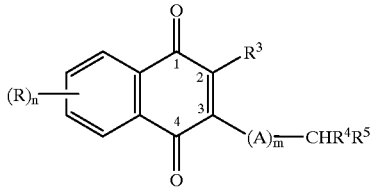

(VII)

wherein m, A and $R^3$, are as defined for formula (I) in claim 1, and $R^4$ and $R^5$ independently represent a $C_{1-7}$ alkyl or haloalkyl group or $C_{2-7}$ alkenyl or haloalkenyl group, in which at least one of $R^4$ and $R^5$ is a haloalkyl group.

23. A compound as claimed in claim 22, wherein A is a $C_{1-4}$ alkylene group and one or both of $R^4$ and $R^5$ is trifluoromethyl.

24. A process for the preparation of a compound of formula (I) comprising reacting an aldehyde corresponding to the group —A—$CHR^4R^5$, where —A— has an aldehyde group at its free end, directly with a compound of formula (V) wherein

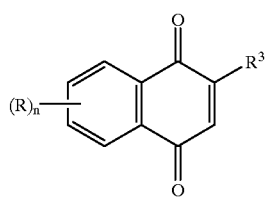

(V)

wherein R, $R^3$ and n are as defined in formula I, in a polar organic solvent under alkaline conditions, and heating the product under acidic conditions in a non-polar solvent to effect elimination of water.

25. A process for the preparation of the compound of formula (I) comprising reacting a compound of the formula (V)

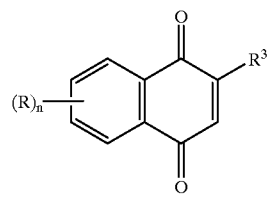

(V)

in which R, $R^3$ and n are defined above, with a carboxylic acid $CHR^4R^5$—$(A)_m$—COOH where $R^4$, $R^5$, m and A are as defined above, in the presence of a free radical initiator.

26. A process for the preparation of a compound of formula (I) comprising reacting a compound of formula (V) with a compound of formula X—$(A)_m CHR^4R^5$ wherein X is a leaving group that will leave the compound to give a charged radical $^+(A)_m$—$CHR^4R^5$ in the presence of an acid.

27. A compound of formula (VIII)

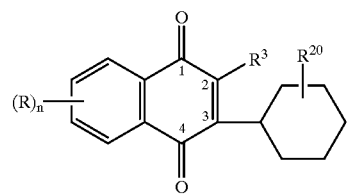

(VIII)

wherein R, n and $R^3$ are as defined for formula (I) in claim 1 and $R^{20}$ is selected from the group consisting of $C_{1-4}$ alkyl, $C_{2-4}$ alkenyl and $C_{2-4}$ haloalkenyl.

28. A compound according to claim 27 wherein $R^{20}$ is methyl.

29. A compound according to claim 27, wherein $R^{20}$ is t-butyl.

30. 2-hydroxy-3-(2-methylcyclohexyl)-naphthalene-1,4-dione.

31. 2-hydroxy-3-(3-methylcyclohexyl)-naphthalene-1,4-dione.

32. 2-hydroxy-3-(4-methylcyclohexyl)-naphthalene-1,4-dione.

33. 2-hydroxy-3-(4-t-butylcyclohexyl)-naphthalene-1,4-dione.

34. A method of combating fungal pests at a locus, which comprises treating the locus with a compound of formula (VIII) as defined in claim 27.

35. A method of combating fungal pests at a locus, which comprises treating the locus with a compound of formula (VI) as defined in claim 21.

36. A method of combating fungal pests at a locus, which comprises treating the locus with a compound of formula (VII) as defined in claim 22.

37. A method as claimed in claim 34 wherein the use is against fungi of Rhizoctonia, Pyricularia and/or Aspergillus.

38. A method as claimed in claim 34 wherein the use is against *R. solani, P. oryzae* or *A. niger*.

39. A method as claimed in claim 35 wherein the use is against fungi of Rhizoctonia, Pyricularia and/or Aspergillus.

40. A method as claimed in claim 35 wherein the use is against *R. solani, P. oryzae* or *A. niger*.

41. A method as claimed in claim 36 wherein the use is against fungi of Rhizoctonia, Pyricularia and/or Aspergillus.

42. A method as claimed in claim 36 wherein the use is against *R. solani, P. oryzae* or *A. niger*.

* * * * *

UNITED STATES PATENT AND TRADEMARK OFFICE

CERTIFICATE OF CORRECTION

PATENT NO.   : 6,043,286
DATED         : March 28, 2000
INVENTOR(S)  : KHAMBAY

It is certified that error appears in the above-identified patent and that said letters patent is hereby corrected as shown below:

On the Title Page, left-hand column, in the section "[30] Foreign Application Priority Data" amend to read --Jan. 10, 1995 [GB] United Kingdom 9500389

Jan. 10, 1995 [GB] United Kingdom 9500394

Jul. 4, 1995 [GB] United Kingdom 9513584

Jul. 4 1995 [GB] United Kingdom 9513594

Nov. 13, 1995 [GB] United Kingdom 9523165--

Signed and Sealed this

Fifteenth Day of May, 2001

Attest:

NICHOLAS P. GODICI

Attesting Officer     Acting Director of the United States Patent and Trademark Office